US 7,147,864 B2

(12) United States Patent
Resnick

(10) Patent No.: US 7,147,864 B2
(45) Date of Patent: *Dec. 12, 2006

(54) METHODS FOR PREVENTING PHOTODAMAGED SKIN BY ADMINISTERING SELEGILINE OR DESMETHYLSELEGILINE

(75) Inventor: Mark G. Resnick, Tampa, FL (US)

(73) Assignee: Somerset Pharmaceuticals, Inc., Tampa, FL (US)

( * ) Notice: Subject to any disclaimer, the term of this patent is extended or adjusted under 35 U.S.C. 154(b) by 104 days.

This patent is subject to a terminal disclaimer.

(21) Appl. No.: 10/806,494

(22) Filed: Mar. 23, 2004

(65) Prior Publication Data

US 2004/0180009 A1  Sep. 16, 2004

Related U.S. Application Data

(63) Continuation of application No. 10/215,492, filed on Aug. 8, 2002, now Pat. No. 6,709,664, which is a continuation of application No. 09/663,218, filed as application No. PCT/US99/04588 on Mar. 3, 1999, now Pat. No. 6,461,619.

(60) Provisional application No. 60/078,043, filed on Mar. 16, 1998.

(51) Int. Cl.
*A61K 6/00* (2006.01)
*A61K 8/00* (2006.01)
*A61F 13/00* (2006.01)

(52) U.S. Cl. .................. 424/401; 424/59; 424/449; 514/654; 514/886; 514/887; 514/870

(58) Field of Classification Search ............... 424/401, 424/59, 449; 514/654, 886, 887, 870
See application file for complete search history.

(56) References Cited

U.S. PATENT DOCUMENTS

| 4,812,481 | A |   | 3/1989  | Reischig et al. ......... 514/647 |
| 4,826,875 | A |   | 5/1989  | Chiesi ..................... 514/534 |
| 4,861,800 | A |   | 8/1989  | Buyske ................... 514/646 |
| 4,868,218 | A |   | 9/1989  | Buyske ................... 514/646 |
| 5,057,321 | A |   | 10/1991 | Edgren et al. ........... 424/413 |
| 5,128,145 | A |   | 7/1992  | Edgren et al. ........... 424/473 |
| 5,190,763 | A |   | 3/1993  | Edgren et al. ........... 424/473 |
| 5,192,550 | A |   | 3/1993  | Edgren et al. ........... 424/473 |
| 5,221,536 | A |   | 6/1993  | Edgren et al. ........... 424/473 |
| 5,242,950 | A |   | 9/1993  | Fries Hastings ........ 514/654 |
| 5,266,332 | A |   | 11/1993 | Dong et al. .............. 424/473 |
| 5,354,885 | A |   | 10/1994 | Milman et al. ............ 560/43 |
| 5,387,615 | A |   | 2/1995  | Milgram et al. ......... 514/654 |
| 5,446,070 | A |   | 8/1995  | Mantelle ................ 514/772.6 |
| 5,744,499 | A | * | 4/1998  | Quash et al. ............ 514/639 |
| 5,783,606 | A | * | 7/1998  | Tatton .................... 514/649 |
| 6,465,440 | B1 | * | 10/2002 | von Borstel et al. ...... 514/45 |
| 6,709,664 | B1 | * | 3/2004  | Resnick .................. 424/401 |

FOREIGN PATENT DOCUMENTS

| EP | 0 404 807 B1 | 6/1993 |
| EP | 0 593 807 A1 | 4/1994 |
| EP | 0 509 761 B1 | 9/1996 |
| WO | WO 95/15160 | 6/1995 |
| WO | WO 96/22068 | 7/1996 |
| WO | WO 97/33572 | 9/1997 |
| WO | WO 99/47133 | 9/1999 |

OTHER PUBLICATIONS

Tatton et al. Modulation of gene expression rather than monoamine oxidase inhibition: (-) deprenyl -related compounds in controlling neurodegenration. Neurology. 1996, vol. 47(6 Suppl. 3):S171-183.*
Darr et al., Topical vitamin C protects porcine skin from ultraviolet radiation-induced damage, British Journal of Dermatology 127:247-253, 1992.
Granger et al., Superoxide Radicals In Feline Intestinal Ischemia, Gastroenterology, 81:22-29, 1981.
Heinonen et al., Pharmacokinetic aspects of I-deprenyl (selegiline) and its metabolites, Clin Pharmacol Ther, 56:742-749, 1994.
Heinonen et al., Pharmacokinetics and metabolism of selegiline, Acta Neurol Scand., 126:93-99, 1989.
Jenner et al., Oxidative stress and the pathogenesis of Parkinson's disease, Neurology, 47(Suppl 3):S161-S170, 1996.
Knoll, Extension of Life Span of Rates by Long-Term (-)Deprenyl Treatment, The Mount Sinai Journal of Medicine, 55(1):67-74, 1988.
Knoll, The Striatal Dopamine Dependency of Life Span in Male Rats. Longevity Study with (-)Deprenyl, Mechanism of Ageing and Development, 46:237-262, 1988.
LaLonde et al., Antioxidants Prevent the Cellular Deficit Produced in Response to Burn Injury, J Burn Care Rehabil, 17:379-383, 1996.
Life Extension Report, Deprenyl Extends the Lifespan of Immunosuppressed Mice, 15(1):1-4, 1995.
Parks et al., Ischemic Injury in the Cat Small Intestine: Role of Superoxide Radicals, Gastroenterology, 82:9-15, 1982.
Schiller et al., Antioxidant therapy, Critical Care Medicine, 21(2):S92-S102, 1993.
Stewart et al., Antioxidant Nutrients Protect Against UVB-Induced Oxidative Damage to DNA of Mouse Keratinocytes In Culture, J Invest Dermatol, 106:1086-1089, 1996.
Carrillo, et al., "(-)Deprenyl Increases Activities of Superoxide Dismutase and Catalase in Certain Brain Regions in Old Male Mice", Life Sciences, vol. 54(14): 975-981, 1994.
Kitani, et al., "(-)Deprenyl Increases the Life Span as Well as Activities of Superoxide Dismutase and Catalase but Not of Gluthathione Peroxidase in Selective Brain Regions in Fischer Rats", Annals of the New York Academy of Sciences, vol. 77:61-71, 1994.

* cited by examiner

*Primary Examiner*—Lakshmi Channavajjala
(74) *Attorney, Agent, or Firm*—Vinston & Elkins LLP

(57) ABSTRACT

The present invention is directed to methods that can be used in the treatment of wounds, burns, and photodamaged skin. Methods can be used for both humans and animals and involve the administration of compositions containing selegiline and/or desmethylselegiline.

23 Claims, No Drawings

METHODS FOR PREVENTING PHOTODAMAGED SKIN BY ADMINISTERING SELEGILINE OR DESMETHYLSELEGILINE

CROSS-REFERENCE TO RELATED APPLICATIONS

The present application is a continuation of U.S. application Ser. No. 10/215,492, filed Aug. 8, 2002, now U.S. Pat. No. 6,709,664, which is a continuation of U.S. application Ser. No. 09/663,218, filed Sep. 15, 2000, now U.S. Pat. No. 6,461,619, which claims priority to international patent application number PCT/US99/04588, filed Mar. 3, 1999, which claims priority to provisional patent application Ser. No. 60/078,043, filed Mar. 16, 1998.

FIELD OF THE INVENTION

The present invention relates to methods for treating wounds, burns, or dermatological damage by administering topical compositions containing selegiline and/or desmethylselegiline.

BACKGROUND OF THE INVENTION

A. Free Radicals

Free radicals are molecules with one or more unpaired electrons in their outer orbitals. The presence of these electrons together with the tendency of molecules to seek the lowest stable energy state causes free radicals to be highly reactive and generally short lived. Among the free radicals commonly found in vivo are oxygen, the superoxide anion and the hydroxyl radical. These are typically referred to as "oxidants" and are often the result of cascades in which electrons are passed from molecule to molecule.

B. Injuries and Free Radical Damage

Injuries such as wounds and burns generate free radicals that have both local and systemic effects. Locally, free radicals have been implicated in both tissue ischemia (Granger, et al., Gastroenterology 81:22–29 (1981); Parks, et al., Gastroenterology 82:9–15 (1982)) and reperfusion injuries (Schiller, et al., Critical Care Med. 21:S92–S100 (1993)). Systemically, burns often cause dysfunction of the heart, lungs and liver. Researchers have found that burn healing is improved when lipid peroxidation (typically caused by the action of free radicals) is reduced (LaLonde, et al., J. Burns Care & Rehabilitation 17:379–383 (1996)).

C. Photodamage

Exposure of skin to electromagnetic radiation in the ultraviolet and visible portions of the spectrum and ionizing radiation may result in damage to both the proteins and the DNA in skin cells. Such "photodamage" has been correlated with the induction of non-melanoma skin cancer, immune function suppression and photoaging.

Exposure of skin to ultraviolet and ionizing radiation and the concomitant pathobiologies have been linked to the generation of oxidants as well as to a reduction in anti-oxidant levels and activity (Stewart, et al., J. Inv. Dermatol. 106:1086–1089 (1996); Darr, et al., Brit. J. Dermatol. 127: 247–253 (1992)). Specifically, research has shown that there is a reduction in epidermal superoxide dysmutase activity and in the levels of vitamin C and vitamin E after exposure to UVB radiation. Elimination of oxidants (e.g., by application of exogenous anti-oxidants) or prevention of oxidant production (e.g., by reduction of exposure to ionizing radiation) can alleviate or prevent dermatological damage. The adverse effects of ionizing radiation include edema, vasodilation, lymphocytic and neutrophilic infiltration in the dermis, dyskeratotic keratinocytes and spongiosis of the epidermis.

D. Use of Anti-Oxidants to Detoxify Free Radicals

A number of different strategies have been used in attempting to prevent or reduce free radical damage. Endogenous anti-oxidants, e.g., superoxide dysmutase, catalase or glutathione peroxidase, may be used to protect cell membranes and agents such as ascorbic acid and glutathione may be used to protect cytosols. Other anti-oxidants, such as alpha-tocopherol and tretinoin, have also been used to ameliorate the effect of free radicals.

Administration of superoxide dysmutase, post-ischemia prevents the increased capillary permeability which accompanies reperfusion injuries (Granger, et al., Gastroenterology 81:22–29 (1981)) and the ablation of free radical generation prior to, and at the time of, reperfusion may prevent or lessen the severity of multiple system organ failure syndrome (Schiller, et al., Critical Care Med. 21:S92–S100 (1993)). Stewart, et al. have shown that UVB-induced DNA damage in human keratinocytes is attenuated by supplementing culture medium surrounding the cells with anti-oxidants such as vitamin C, selenite, or a water-soluble vitamin E analog (J. Inv. Dermatol. 106:1086–1089 (1996)).

E. Selegiline and Desmethylselegiline

Monoamine oxidase A (MAO-A) and monoamine oxidase B (MAO-B) are enzymes found in both in the central nervous system and in peripheral tissues. MAO-A and MAO-B catalyze the oxidative deamination of primary amines, including neuroactive and vasoactive amines, resulting in the formation of toxic free radical species and free radical-generating cascades. Selegiline is a potent and selective inhibitor of monoamine oxidase B and has been reported to have an action in protecting or rescuing neurons of the central nervous system (Knoll, Mount Sinai J. Med. 55:67–74 (1988)). Although the exact mechanism by which selegiline causes its effects is not known, there is evidence suggesting that it may provide neuroprotection or neuronal rescue by reducing oxidative damage caused by monoamine oxidase and/or other oxidants (Jenner, et al., Neurology 47:S162–S170 (1996)). In this regard, selegiline has been shown to increase the activity of the endogenous anti-oxidants superoxide dysmutase, catalase and glutathione peroxidase (Id.).

Desmethylselegiline, one of the metabolites of selegiline, exhibits reduced MAO-B inhibitory activity in comparison to selegiline and its activity with respect to the inhibition of MAO-A is decreased to an even greater extent. Thus, it is expected that desmethylselegiline should produce selegiline-like neuroprotective effects with a decreased risk of side effects associated with MAO-A inhibition.

Although selegiline has been used to treat Parkinson's disease, its use as a treatment for injuries, such as burns and wounds, and for alleviating dermatological damage, such as photodamage, has not been known heretofore. The present invention is directed to methods which rely upon the administration of selegiline or desmethylselegiline to speed the healing and reduce the complications associated with these conditions.

SUMMARY OF THE INVENTION

The present invention is based upon the discovery that compositions comprising selegiline and/or desmethylselegiline can be used in the treatment of wounds, burns and photodamaged skin. In the case of burns and wounds, compositions should be administered for a duration sufficient to promote epithelization. In the case of photodamaged skin, the composition should be administered for a duration sufficient to promote healing, as evidenced by a reduction in one or more of the symptoms associated with photodamaged skin. These symptoms include edema, vasodilation, lymphocytic and neutrophilic infiltration in the dermis, dyskeratotic keratinocytes and spongiosis of the epidermis.

Although the invention encompasses administration by any route, delivery by means of a topical composition containing between $1 \times 10^{-11}$ moles/liter and $1 \times 10^{-3}$ moles/liter of selegiline and/or desmethylselegiline is preferred. Topical compositions may be delivered by means of a spray, patch, salve, cream, lotion or gel. As used herein, the term "desmethylselegiline" refers to either the R(−) enantiomeric form of the drug, the S(+) enantiomeric form of the drug, or a racemic mixture of the two. In carrying out the present methods, the R(−) enantiomer maybe used in the substantial absence of the S(+) enantiomer or vice versa. An enantiomer is substantially absent if it constitutes less than 10% of the combined desmethylselegiline enantiomers. Compositions may contain water, suspending agents, thickeners, humectants, preservatives, emollients, emulsifiers and film formers. They may be applied either directly to the skin of a patient or they may be applied as part of a patch.

Although not preferred, non-topical routes of administration are compatible with the present invention and may be used. The dosage of selegiline or desmethylselegiline when used non-orally should be at least 0.015 mg per kg body weight, calculated on the basis of the free secondary amine, with progressively higher doses being employed depending upon the route of administration and the subsequent response to therapy. Typically, the daily non-oral dose will be about 0.10 mg/kg and may extend to about 1.0 mg/kg (all such doses again being calculated on the basis of the free secondary amine).

DETAILED DESCRIPTION OF THE INVENTION

In the following description, reference will be made to various methodologies well known to those skilled in the art of medicine and pharmacology. Such methodologies are described in standard reference works setting forth the general principles of these disciplines. Unless otherwise indicated, the descriptions apply to selegiline, and all enantiomeric forms of desmethylselegiline.

Dosage

The optimal daily dose of selegiline and/or desmethylselegiline useful for the purposes of the present invention may be determined by methods known in the art based upon clinical conditions such as the severity of the injury, the condition of the subject to whom treatment is being given, the desired therapeutic response and the concomitant therapies being administered to the patient or animal. Ordinarily, however, it is expected that the attending physician or veterinarian will apply a topical composition containing a concentration of selegiline and/or desmethylselegiline between $1 \times 10^{-11}$ moles/liter and $1 \times 10^{-3}$ moles/liter, preferably between $1 \times 10^{-9}$ moles/liter and $1 \times 10^{-3}$ moles/liter. Sufficient composition should be administered to completely cover the damaged area on the individual's skin.

If the physician chooses non-oral routes of administration, at least 0.015 mg/kg of selegiline and/or desmethylselegiline should be administered daily with the more typical dosage being about 0.10 mg/kg. The daily dosage may be increased up to about 1.0 mg/kg. In all cases, doses are calculated on the basis of the free secondary amine form of the agent being administered. These guidelines further require that the actual dosage be carefully titrated by the attending physician or veterinarian depending upon the age, weight, clinical condition and observed response of the individual being treated.

Topical compositions can be applied several times during the day to wounded, burned or photodamaged skin. Similarly, daily dosages of non-oral preparations may be administered in a single or multiple dosage regiment. In addition, dosage forms permitting the continuous release of active agent, e.g., a transdermal patch, may be used for delivering drug.

Dosage Forms Route of Administration

As noted above, topical administration and topical dosage forms are generally preferred for the present methods. However, any of the numerous dosage forms described in the literature for the administration for selegiline may be used and may include desmethylselegiline as desired. For example, U.S. Pat. No. 4,812,481 discloses the use of selegiline, in combination with amantadine, in oral, pectoral, internal, pulmonary, rectal, nasal, vaginal, lingual, intravenous, intraarterial, intracardial, intramuscular, intraperitoneal, intracutaneous, and subcutaneous formulations. Dosage forms for selegiline having an outer wall with one or more pores in the wall impermeable to selegiline but permeable to external fluids have been described. This dosage form may have applicability for oral, sublingual, or buccal administration. Similarly, a variety of selegiline compositions, including tablets, pills, capsules, powders, aerosols, suppositories, skin patches, parenterals, and oral liquids, including oil suspensions, solutions and emulsions have been described. Further disclosed are selegiline-containing sustained release (long acting) formulations and devices.

Topical dosage forms may be prepared according to conventional techniques with creams being generally preferred. The topical cream may be a cosmetically elegant oil in water, cream/lotion/emulsion, containing the desired specified concentration of selegiline and/or desmethylselegiline. Such moisturizing cream formulations may contain a vehicle, a buffer system to maintain the vehicle at an appropriate pH, and an acceptable antimicrobial preservative system. The cream may further contain thickeners, humectants, emollients, emulsifiers and film formers. Methods for preparing appropriate formulations are well known in the art (see e.g., Remington's Pharmaceutical Sciences, 16th ed., A. Oslo. ed., Easton Pa. (1980)).

Transdermal dosage forms can be prepared utilizing a variety of techniques that have been described in the art. Examples may be found in U.S. Pat. Nos. 4,861,800; 4,868,218; 5,128,145; 5,190,763; and 5,242,950; and in foreign patent documents EP-A 404807; EP-A 509761; and EP-A 593807. A monolithic patch structure can be utilized in which drug is directly incorporated into the adhesive and this mixture is cast onto a backing sheet. EP-A 593807 describes a composition in which selegiline is administered as an acid addition salt by incorporating it into a multi layer patch which promotes a conversion of the salt into the free base form of selegiline. One can also employ a device using a lyotropic liquid crystalline composition in which, for example, 5–15% of selegiline is combined with a mixture of liquid and solid polyethylene glycols, a polymer and a non-ionic surfactant, optionally with the addition of propylene glycol and an emulsifying agent. Further details on the preparation of such transdermal formulations, are found in the patent literature.

Buccal and sublingual dosage forms of selegiline and/or desmethylselegiline may be prepared utilizing techniques described in, for example, U.S. Pat. Nos. 5,192,550; 5,221,536; 5,266,332; 5,057,321; 5,446,070; or 5,354,885.

Chemical Form of Selegiline or Desmethylselegiline

The present invention is not limited to any particular form of selegiline and/or desmethylselegiline and drugs may be used either as free bases or as pharmaceutically acceptable acid addition salts. In the latter case, the hydrochloride salt is generally preferred. However, other salts derived from organic and inorganic acids may also be used.

Manner of Treatment

The methods disclosed herein may be used for both human and nonhuman subjects. With regard to the latter, the methods are particularly, but not exclusively, directed to domesticated mammals such as canine and feline species.

In the case of wounds and burns, treatment by administration of selegiline and/or desmethylselegiline should be continued until epithelialization is complete. For dermatological damage, treatment should be continued until the related symptoms, such as edema, vasodilation, lymphocytic and neutrophilic infiltration or spongiosis of the epidermis, subside. The drugs may be either administered at regular intervals (e.g., twice a day) or in an essentially continuous manner (e.g. via a transdermal patch).

EXAMPLES

Example 1

Protective Effects of Selegiline and Desmethylselegiline Against Photodamage

The ability of selegiline and/or desmethylselegiline to prevent photodamage can be correlated to the reduction of cell apoptosis following exposure to UVB radiation. Previous research has shown that primary human keratinocytes grown in serum-free medium are susceptible to UVB-induced apoptosis when exposed to 600–800 J/m2. In addition, deprivation of growth factors, specifically insulin, increases keratinocyte sensitivity to UVB radiation with apoptosis occurring at UVB levels of 200 J/m2.

Two sets of primary human keratinocytes are grown in complete, and growth factor deprived (GFD) media for a total of four sets of cultures. The keratinocytes are then placed in GFD or complete media containing 0, $1\times10^{-9}$, $1\times10^{-8}$, $1\times10^{-7}$, $1\times10^{-5}$, $1\times10^{-6}$, $1\times10^{-4}$, and $1\times10^{-3}$ M selegiline or desmethylselegiline. Twenty-four hours after the addition of the drugs, the keratinocytes grown in GFD medium are irradiated with zero or 200 J/m2 UVB and the keratinocytes grown in complete media are irradiated with zero or 800 J/m2 UVB. Using morphological examination, DAPI staining, Annexin V-FITC FACS analysis and PARP cleavage analysis, the keratinocytes are tested for apoptosis. 15 hours after irradiation.

First, the keratinocytes are examined for morphological signs of apoptosis. Following morphological examination, the cells are harvested by trypsinization and pelleted by low speed centrifugation. Each pellet is divided into three parts for the remaining evaluation.

DAPI staining is used to examine the cells for nuclear condensation characteristic of cell apoptosis. An aliquot of each cell pellet is washed with PBS, fixed in Histochoice, and resuspended in DAPI staining solution for one hour. The cells are subsequently washed in PBS and attached to microscope slides by cytospins. The cells are then visualized by epifluorescent microscopy and the percentage of apoptotic cells determined.

Annexin V-FIT FACS analysis is used to determine extracellular phosphatidylserine exposure. In the early stages of cell apoptosis, portions of the plasma membrane translocate causing the normally intracellular phosphatidylserine to move to the extracellular surface of the plasma membrane. Annexin V binds to the extracellular phosphatidylserine and the amount of such binding is measured by flow cytometry. An aliquot of each cell pellet is washed in PBS and resuspended in a binding buffer. The cells are then incubated in the dark for 15 minutes in the presence of Annexin V-FIT and propidium iodide. Following incubation, the percentage of apoptotic cells is determined using FACS analysis. Apoptotic cells are Annexin V-FACS positive and propidium iodide negative.

PARP cleavage analysis is used to measure the proteolytic cascade which occurs during apoptosis. One of the substrates for apoptosis-related proteases is poly(ADP-ribose) polymerase, or PARP. After cleavage, PARP reduces to a characteristic 85 kD fragment. An aliquot of each cell pellet is resuspended in RIPA buffer containing 7% urea and protein lysates. The resulting cell proteins are then transferred to Immobilin P membranes by semi-dry electrophoresis and incubated in TSB buffer (150 mM sodium chloride; 100 mM Tris-base, pH 7.5; 2% blocking reagent B: Boehringer Mannheim) for 2 hours at room temperature. Anti-PARP monoclonal antibodies (clone C-2-10) are diluted in TSB and 2% blocking reagent B. Following one hour of incubation, the membrane is washed three times with TSB buffer containing 0.1% Tween20. After the incubation is completed, biotinylated goat (Fab'-fragments) anti-mouse Ig diluted in TSB is added to the membrane and the membrane is then washed three times with TSB buffer containing 0.1% Tween20. A streptavidin-horseradish peroxidase conjugate is added to the membrane and the protein bands are visualized using Enhanced Chemiluminescent Plus (Amersham). The percent of PARP cleavage is determined using densitometry to compare the total PARP protein with the cleaved PARP fragment (85 kD).

Example 2

Curative Effects of Selegiline and Desmethylselegiline on Burns

The ability of selegiline and desmethylselegiline to assist in the healing of burns was tested using a second-degree burn wound model. In second-degree burns, the entire surface of the epidermis is destroyed. An epidermal covering is regenerated from the remaining epithelial and epidermal cells adjacent to the burns. This phase of the healing process is called epithelization.

A. Materials and Methods

Experimental Animals

Swine were used for the experimental research animal because their skin has many morphological similarities to human skin. Seven young female specific pathogen free (SPF:Ken-O-Kaw Farms, Windsor, Ill.) pigs weighing 25–30 kg were kept in house for two weeks prior to initiating the experiment. These animals were fed a basal diet ad libitum and housed individually in facilities with controlled temperature (19–21° C.) and lights (12 h/12 h LD).

Wounding Technique

Experimental animals were clipped with standard animal clippers on the day of the experiment. The skin on the back and both sides of the animal was prepared for wounding by washing with a non-antibiotic soap and sterile water. Each animal was anesthetized i.m. with ketamine-HCl (20 mg/kg), xylazine (2 mg/kg) and atropine (0.05 mg/kg), followed by mask inhalation of an isoflurane and oxygen combination. Five specifically designed cylindrical brass rods weighing 358 g each were heated in a boiling water bath to 100° C. A rod was removed from the water bath and wiped dry before being applied to the skin surface to prevent water-droplets from creating a steam burn on the skin. The brass rod was held at a vertical position on the skin for six seconds with all pressure being supplied by gravity in order to make a burn 8.5 mm diameter×0.8 mm deep. Immediately after burning, the roof of the burn blister was removed with a sterile spatula. The burn wounds were made approximately 2 cm from each other.

Approximately 90 burn wounds were made on the anterior two-thirds of the animal. The posterior third of the animal cannot be used because of anatomical differences in burn wound healing (a more rapid healing of burns has been observed at that position). Burn wounds were randomly assigned to seven treatment groups and were applied in the pattern shown in Table 1.

TABLE 1

Treatment Groups

| Number of Animals | Treatment Groups | | |
|---|---|---|---|
| 1 | agent A (dose X) | agent A (dose Y) | agent A (dose Z) |
| 1 | agent A (dose Y) | agent A (dose Z) | agent B (dose X) |
| 1 | agent A (dose Z) | agent B (dose X) | agent B (dose Y) |
| 1 | agent B (dose X) | agent B (dose Y) | agent B (dose Z) |
| 1 | agent B (dose Y) | agent B (dose Z) | air exposed, control |
| 1 | agent A (dose X) | agent B (dose Z) | air exposed, control |
| 1 | agent A (dose X) | agent A (dose Y) | air exposed, control | agent A = selegiline
agent B = desmethylselegiline HCL
dose X = $10^{-4}$ M
dose Y = $10^{-6}$ M
dose Z = $10^{-8}$ M A total of seven animals were used and a total of fifteen wounds per treatment group were analyzed on each of days 7–12 after wounding. Treatments were coded to maintain blind study compliance. The burn wounds were treated with 25 ug of test article (enough to cover each wound). Treatments were allowed to penetrate into the sites for at least a 20 minute time period. Each treatment was applied within 20 minutes of blister removal and treatment occurred once a day for the first five days.

Epidermal Migration Assessment

Beginning on day seven after wounding (day 0) and each day thereafter for four to six days, five burn wounds and the surrounding normal skin from each treatment area were excised using an electrokeratome. Any specimens that were not excised intact were discarded. The excised wounds and the surrounding normal skin were incubated in 0.5 M NaBr for 24 hours at 37° C. After incubation, the specimens were separated into epidermal and dermal sheets. The epidermis was examined macroscopically for defects in the area of the burn wounds. Epithelization was considered complete if no defect was present (healed). Any defect in the burn area indicated that healing was incomplete. The epidermal sheet was placed on cardboard for a permanent record.

B. Result

After the study was completed, the codes were revealed and data was tabulated. The number of wounds healed (completely epithelized) were divided by the total number of wounds sampled per day and multiplied by 100. Results are shown in Table 2.

TABLE 2

Epithelization Results (combined data)*

| TREAT-MENT | DAYS AFTER BURNING | | | | | | |
|---|---|---|---|---|---|---|---|
| | 7 | 8 | 9 | 10 | 11 | 12 | 13 |
| Saline Control | 0/15 (0%) | 0/15 (0%) | 0/15 (0%) | 0/15 (0%) | 5/15 (33%) | 6/15 (40%) | 10/15 (67%) |
| A-1 | 0/15 (0%) | 0/15 (0%) | 0/15 (0%) | 3/15 (20%) | 5/15 (33%) | 6/15 (40%) | 6/15 (40%) |
| A-2 | 0/15 (0%) | 0/15 (0%) | 0/15 (0%) | 3/15 (20%) | 5/15 (33%) | 6/15 (40%) | 6/15 (40%) |
| A-3 | 0/15 (0%) | 0/15 (0%) | 0/15 (0%) | 0/15 (0%) | 0/15 (0%) | 1/15 (7%) | 6/16 (38%) |
| B-1 | 0/15 (0%) | 0/15 (0%) | 0/15 (0%) | 0/15 (0%) | 1/15 (7%) | 5/15 (33%) | 11/16 (69%) |
| B-2 | 0/15 (0%) | 0/15 (0%) | 0/15 (0%) | 0/15 (0%) | 5/15 (33%) | 7/15 (47%) | 6/16 (100%) |
| B-3 | 0/15 (0%) | 0/15 (0%) | 0/15 (0%) | 0/15 (0%) | 5/15 (33%) | 10/15 (67%) | 10/15 (67%) |

*Wounds are presented as the number of wounds healed (completely epithelized) over the number of wounds assessed.
( ) Percent of wounds completely epithelized
Code:
A = selegiline HCL;
B = desmethylselegiline HCL
1 = 10-4 M
2 = 10-6 M
3 = 10-8 M All wounds absorbed the administered compounds within 10 to 15 minutes of application. During the first three days of treatment, the wound crust in all treatment groups turned a white color during absorption of applied agent. This was more pronounced with treatments A and B. After 15 minutes, the crust's color became normal again. Neither residue, erythema or infection were observed in any treatment groups. The results shown in Table 2 may be summarized as follows:

Day 7–9: None of the burn wounds were completely epithelized.

Day 10: Twenty percent (20%) of wounds which were treated with selegiline HCl at concentrations of 1×10-4 M and 1×10-6 M were completely epithelized. None (0%) of the wounds from any other treatment groups were completely epithelized.

Day 11: Thirty-three percent (33%) of wounds treated with either selegiline HCl (10-4 M and 10-6M), desmethylselegiline HCl (10-6 M and 10-8M), or saline were completely epithelized. Seven percent (7%) of the desmethylselegiline HCl (10-4M) treated wounds were completely epithelized. None of the wounds treated with selegiline HCl (10-8 M) were completely epithelized.

Day 12: Thirty-three percent (33%) and forty percent (40%) of wounds treated with selegiline HCl (10-4 M and 10-6 M respectively), were completely epithelized. Only seven percent (7%) of wounds treated with the 10-8M concentration of selegiline HCl were completely epithelized. Thirty-three percent (33%), forty-seven percent (47%) and sixty-seven percent (67%) of wounds treated with desmethylselegiline HCl (10-4M and 10-6M and 10-8M respectively) were completely epithelized. Forty percent (40%) of wounds treated with saline, i.e., the control cells, were completely epithelized.

Day 13: Thirty-three (33%) and forty (40%) percent of wounds treated with selegiline HCl (10-4M and 10-6M respectively) were completely epithelized. Thirty-eight percent of wounds treated with the 10-8 M concentration of selegiline HCl were completely epithelized. Sixty-nine (69%), one hundred (100%) and sixty-seven (67%) percent of wounds treated with desmethylselegiline HCl (10-4 M, 10-6 M, and 10-8 M respectively) were completely epithelized. Sixty-seven (67%) percent of wounds treated with saline, i.e., controls, were completely epithelized.

C. Discussion

The data from these studies suggest that the wounds treated with selegiline HCl (10-4 M and 10-6 M) were able to initiate epithelization at an earlier time point than all other treatment groups. However, wounds treated with desmethylselegiline HCl (all concentrations) had a higher percentage of wounds completely epithelized on day thirteen. Wounds treated with desmethyl-selegiline HCl (10-6 M) were completely epithelized sooner than all other treatment groups.

Example 3

Use of Selegiline and Desmethylselegiline to Improve Appearance of Photodamaged Skin The test subjects, human females exhibiting moderate to severe photoaging on the dorsal portions of their forearms and hands, are randomly assigned to receive either vehicle plus selegiline or vehicle alone. For a period of 16 weeks, the test subjects apply sufficient cream to cover the designated test area BID. Clinical assessments of the appearance of the test area are made prior to administration of the cream and at the second, eighth, sixteenth and twenty-fourth weeks.

Example 4

Use of Selegiline to Preserve the Positive Effects of Tretinoin on Photoaged Skin The test subjects, human females exhibiting moderate to severe photoaging on the face and dorsal portions of their forearms, are randomly assigned to apply either the vehicle plus selegiline combination or vehicle alone. For an initial period of sixteen weeks, all test subjects treat bilateral aspects of their face, forearms and hands with a tretinoin cream once per day. For a subsequent one week period, all test subjects use no treatment on the test areas. For the following sixteen week period, the test subjects apply cream, either containing vehicle alone or vehicle plus selegiline to cover one half of the designated area BID. Clinical assessments of the test areas are made prior to the administration of the cream and throughout the study.

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A method of preventing or reducing photodamage to skin cells of a subject comprising administering a composition comprising selegiline and/or desmethylselegiline to the subject in an amount effective to reduce apoptosis of skin cells exposed to electromagnetic or ionizing radiation.

2. The method of claim 1, wherein the composition is a topical composition.

3. The method of claim 2, wherein the topical composition is in a form selected from the group consisting of a cream, gel, transdermal patch, salve, lotion, and spray.

4. The method of claim 2, wherein the topical composition comprises selegiline at a concentration of between $1 \times 10^{-11}$ moles/liter and $1 \times 10^{-11}$ moles/liter.

5. The method of claim 2, wherein the topical composition comprises desmethylselegiline at a concentration of between $1 \times 10^{-11}$ moles/liter and $1 \times 10^{-3}$ moles/liter.

6. The method of claim 1, wherein the composition comprises desmethylselegiline in the form of its R(-) enantiomer and the S(+) enantiomer is substantially absent.

7. The method of claim 1, wherein the composition comprises desmethylselegiline in the form of its S(+)enantiomer and the R(-) enantiomer is substantially absent.

8. The method of claim 1, wherein the composition further comprises a diluent or carrier comprising one or more compounds selected from the group consisting of water, suspending agents, thickeners, humectants, preservatives, emollients, emulsifiers, and film formers.

9. The method of claim 1, wherein the selegiline is administered as the free base.

10. The method of claim 1, wherein the selegiline is administered as a pharmaceutically acceptable acid addition salt.

11. The method of claim 1, wherein the desmethylselegiline is administered as the free base.

12. The method of claim 1, wherein the desmethylselegiline is administered as a pharmaceutically acceptable acid addition salt.

13. A method of treating a subject for photodamaged skin, wherein the photodamage results from exposure to electromagnetic or ionizing radiation, comprising administering a topical composition comprising selegiline and/or desmethylselegiline to the skin of the subject in an amount effective to reduce oxidative damage resulting from exposure to electromagnetic or ionizing radiation.

14. The method of claim 13, wherein the topical composition is in a form selected from the group consisting of a cream, gel, transdermal patch, salve, lotion, and spray.

15. The method of claim 13, wherein the topical composition comprises selegiline at a concentration of between $1 \times 10^{-11}$ moles/liter and $1 \times 10^{-3}$ moles/liter.

16. The method of claim 13, wherein the topical composition comprises desmethylselegiline at a concentration of between $1 \times 10^{-11}$ moles/liter and $1 \times 10^{-3}$ moles/liter.

17. The method of claim 13, wherein the topical composition comprises desmethylselegiline in the form of its R(-) enantiomer and the S(+) enantiomer is substantially absent.

18. The method of claim 13, wherein the topical composition comprises desmethylselegiline in the form of its S(+)enantiomer and the R(-) enantiomer is substantially absent.

19. The method of claim 15, wherein the topical composition further comprises a diluent or carrier comprising one or more compounds selected from the group consisting of water, suspending agents, thickeners, humectants, preservatives, emollients, emulsifiers, and film formers.

20. The method of claim 15, wherein the selegiline is administered as the free base.

21. The method of claim 15, wherein the selegiline is administered as a pharmaceutically acceptable acid addition salt.

22. The method of claim 15, wherein the desmethylselegiline is administered as the free base.

23. The method of claim 15, wherein the desmethylselegiline is administered as a pharmaceutically acceptable acid addition salt.

* * * * *

UNITED STATES PATENT AND TRADEMARK OFFICE
CERTIFICATE OF CORRECTION

| | |
|---|---|
| PATENT NO. | : 7,147,864 B2 |
| APPLICATION NO. | : 10/806494 |
| DATED | : December 12, 2006 |
| INVENTOR(S) | : Mark G. Resnick |

It is certified that error appears in the above-identified patent and that said Letters Patent is hereby corrected as shown below:

Column 9, line 58, after "of" delete "preventing or".

Signed and Sealed this

Seventeenth Day of April, 2007

JON W. DUDAS
*Director of the United States Patent and Trademark Office*